United States Patent
Grund et al.

(10) Patent No.: US 6,752,799 B2
(45) Date of Patent: Jun. 22, 2004

(54) METHOD AND DEVICE FOR ENDOSCOPIC INJECTION OF AT LEAST ONE FLUID

(75) Inventors: Karl Ernst Grund, Tübingen (DE); Günter Farin, Tübingen (DE); Dogan Özmen, Iserlohn (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 0 days.

(21) Appl. No.: 09/142,375

(22) PCT Filed: Feb. 28, 1997

(86) PCT No.: PCT/EP97/01039

§ 371 (c)(1),
(2), (4) Date: Mar. 15, 1999

(87) PCT Pub. No.: WO97/31667

PCT Pub. Date: Sep. 4, 1997

(65) Prior Publication Data

US 2003/0065306 A1 Apr. 3, 2003

(30) Foreign Application Priority Data

Mar. 1, 1996 (DE) .......................... 196 07 922

(51) Int. Cl.[7] .............................................. A61M 31/00
(52) U.S. Cl. ...................................... 604/508; 604/514
(58) Field of Search ............................ 604/151, 11, 19, 604/27, 28, 506, 508, 514, 67, 70, 118

(56) References Cited

U.S. PATENT DOCUMENTS

| 4,468,216 A | * | 8/1984 | Muto .......................... 604/43 |
| 4,898,574 A | * | 2/1990 | Uchiyama et al. ............. 604/22 |
| 5,087,244 A | * | 2/1992 | Wolinsky et al. ............ 604/509 |
| 5,116,313 A | | 5/1992 | McGregor |
| 5,279,542 A | * | 1/1994 | Wilk ........................... 600/157 |
| 5,702,384 A | * | 12/1997 | Umeyama et al. ........... 604/173 |
| 5,840,061 A | * | 11/1998 | Menne et al. .................. 604/68 |

FOREIGN PATENT DOCUMENTS

| EP | 0 398 583 A1 | 11/1990 |
| SU | 831114 | 5/1981 |
| WO | WO 96/36381 | 11/1996 |
| WO | WO 97/31667 | 4/1997 |

* cited by examiner

Primary Examiner—Brian L. Casler
Assistant Examiner—Kevin C. Sirmons
(74) Attorney, Agent, or Firm—St. Onge Steward Johnston & Reens LLC

(57) ABSTRACT

It is very difficult to carry out injections during endoscopic operations. Here it is proposed to expel a specified amount of fluid from the end of a tube or from a nozzle, with hydraulic parameters such as pressure, rate of pressure increase, duration and/or velocity that can be adjusted to specified values, and with energy such that after traveling a distance between the tube end or the nozzle and the tissue in substantially free flight, the fluid penetrates into the tissue.

4 Claims, 5 Drawing Sheets

METHOD AND DEVICE FOR ENDOSCOPIC INJECTION OF AT LEAST ONE FLUID

FIELD OF THE INVENTION

Background

The invention relates to a method of endoscopically injecting at least one fluid and an apparatus with which to implement the method.

During endoscopic operations a great variety of manipulations are undertaken in natural or artificial cavities in the body, in the course of which it repeatedly becomes necessary to remove tissues and/or stop bleeding. Among the techniques used here are forms of injection. For example, a polyp on a sufficiently long stalk can be removed relatively simply (by catching it in a noose), but this is not possible in the case of so-called sessile polyps, which are merely small elevations in the tissue. In such cases it is necessary to raise the polyps, by injecting fluid, in particular physiological saline, into the underlying tissue by means of an injection needle. A sessile polyp raised in this way can then be removed with the known techniques.

A different occasion for the injection of fluids arises when bleeding must be stanched. One way to stop bleeding is to inject physiological saline so as to form a depot around a blood vessel and thereby close it mechanically. Alternatively, a corresponding effect can be achieved by the injection of medications, in particular vasoconstrictive substances. Another means of stopping bleeding is the injection of fibrin adhesives.

Finally, yet another application of injections should be mentioned, namely the marking of operation or treatment sites. Often after a treatment such as the removal of a growth in the intestine, the affected site must be inspected at regular intervals in order to monitor the result of the treatment or the healing process. In particular when the operation site covers a small area and healing is progressing well, it is very difficult to find the treated site again. For this purpose it is useful to stain the treated site or to place marking dots in its vicinity.

The object of the invention is to disclose a method and an apparatus by means of which fluids can be injected during endoscopic operations.

To solve the problem cited above a method is disclosed for the endoscopic injection of at least one fluid, in particular a solution, a suspension or an emulsion or a mixture of several solutions, into a tissue in a hollow organ, a body cavity or an artificial cavity in a human or animal body. In this process a specified amount of fluid is expelled from the end of a tube or from a nozzle with specifiably adjustable hydraulic parameters such as pressure, rate of rise of pressure, duration and velocity of fluid flow, and with energy such that after an essentially free flight across a distance separating the tube end or nozzle from the tissue, the fluid penetrates into the tissue. That is, in the method in accordance with the invention (or in the apparatus in accordance with the invention) no injection needle is used, which would have to be inserted into the tissue to which the liquid is to be applied. This property makes the method in accordance with the invention especially suitable for the application of fluids during endoscopic operations. In particular, the hydraulic parameters can be adjusted so as to ensure that the fluid penetrates the tissue down to a specified depth, at which the fluid can then exert the desired effect. As a result, it also becomes considerably more certain that undesirable effects will be avoided. For instance, when a site in the intestine is to be marked, it is extremely dangerous to operate with an injection needle, because it is very easy to pierce through the intestinal wall. When the method in accordance with the invention is used, this danger is considerably less.

The preferred procedure is not to apply the entire amount of fluid to be injected in a single "portion". Instead, the desired amount of fluid is injected as a plurality of minimal amounts, all of substantially the same size. The result is to ensure that essentially any desired total amount of fluid can be injected, while nevertheless keeping constant the hydraulic parameters, i.e. the parameters that determine the depth of injection, the diameter of the opening formed in the tissue, and so on; the outcome of the injection process is therefore optimal.

The fluid is preferably not injected perpendicularly into the tissue (i.e., perpendicular to its surface), but rather at an angle. This angle is preferably 30° to 60° with respect to the tissue. Surprisingly, this range has been found to give the best injection results.

Where possible, the fluid is injected in such a thin stream that the hole formed in the tissue during injection closes immediately thereafter, so that practically none of the injected fluid is then released. This can readily be achieved, because when a correspondingly large number of single (individually small) portions is injected, the amount of fluid can be made as large as desired even though the stream of fluid is very thin.

When two different fluids that can react with one another are to be applied, such as the above-mentioned fibrin adhesive or the like, the fluids are preferably not mixed until just before they injected together, or they are injected separately in rapid succession (in small portions as described above) at the same site, in such a way that they become mixed at the injection site. Especially in the case of fluid mixtures, the individual components of which react with one another very rapidly, and in particular solidify or adhere together, this method of successive injection of fluids is an excellent means of preventing a reaction from taking place in the injection apparatus itself (nozzle or end of tube) and hence destroying the apparatus.

A certain problem can be presented by the unintended emergence of fluid from the end of the tube. This is of no importance when the fluid is a physiological saline solution to be injected underneath a polyp. However, if it is a marking fluid such as tattooing ink, accidental leakage from the end of the tube has fatal consequences, because a place is marked that should not be marked at all. It would be equally fatal if medications were to leak out accidentally. However, some leakage cannot be avoided, if only because a tube filled to its distal end and positioned in the working channel of the endoscope changes its volume—although only slightly—as the endoscope moves, so that some liquid emerges. It is now proposed to suck away fluid that emerges unintentionally from the end of the tube. This action is made particularly simple by generating a continuous suction current, such that the volume it withdraws per unit time is smaller than the volume injected per unit time during the injection process. By this means, it is ensured that the slowly, unintentionally emerging fluid is completely sucked away, whereas the amount of fluid emerging at high velocity, with a relatively high volume flow per unit time, is practically not reduced.

SUMMARY OF THE INVENTION

The endoscopic injection apparatus in accordance with the invention, designed to inject at least one fluid, in particular a solution, a suspension or an emulsion or a mixture thereof into a tissue in a hollow organ, a body cavity or an artificial cavity in a human or animal body, comprises a tube with a distal and a proximal end, which can be so inserted through a working channel of an endoscope, or is so incorporated into an endoscope, that the distal end of the tube projects out of a distal end of the endoscope or ends substantially at the end of the endoscope. A pump mechanism is provided that is in sealed connection with the proximal end of the tube and is so constructed that in response to a control signal it expels from the distal end of the tube a specified amount of fluid, with hydraulic parameters such as pressure, rate of pressure increase, duration and/or velocity that can be set to specified values, and with sufficient energy that the fluid penetrates into the tissue.

The distal end of the tube in this arrangement is preferably so shaped, or provided with a nozzle in such a way, that the hole formed in the tissue during injection closes of its own accord, without previously allowing any appreciable amount of injected fluid to escape. To achieve this, the diameter of the tube end or the nozzle is preferably very small.

The pump mechanism is preferably so constructed that a desired amount of fluid can be injected as a plurality of small, consecutively injected individual volumes. It is therefore necessary that the pump be able to expel very small volumes of fluid one after another in a relatively short time.

Preferably aiming and/or positioning devices are provided at the distal end of the tube, so that the distal end can be kept at a predetermined distance from the tissue and/or oriented in a predetermined direction with respect to the tissue. Preferably these aiming and/or positioning devices are so constructed that the fluid can be injected into the tissue at an angle of about 30° to 60°. That is, the aiming devices for this case must be so constructed that the person operating the apparatus can estimate the angle at which the nozzle or the tube end is directed toward the surface of the tissue.

For special applications the tube, at least in its distal section, comprises several, in particular two lumina. The pumping mechanisms comprise several individual pumps, in order to inject several, in particular two fluids so that they become mixed. This arrangement is useful, for example, when two-component adhesives such as fibrin adhesive are to be injected.

In a further embodiment of the invention the tube preferably comprises a gas- and/or liquid-return lumen, which opens into the tube at its distal end in such a way that the fluid contained in the tube is prevented from emerging through the distal end. For this purpose it is advantageous to provide a suction device to suck fluid out of the fluid-return lumen, which is substantially permanently in operation. This suction device can, for example, be a suction extractor of the kind often present in an operating theatre.

In a preferred embodiment the tube comprises, at or near its distal end, a section with a single lumen or a nozzle, which both facilitates the conduction of such fluid as emerges and, in case two different fluids are to be expelled, enables them to be mixed while still in the tube or the nozzle.

The tube is preferably made of such material, and is sufficiently resistant to pressure and/or provided with sufficient stiffening means, that a pressure pulse introduced into its proximal end emerges essentially undamped or unchanged from its distal end. In this regard it is also important to choose a material with only slight internal damping. The tube can be so constructed that it allows passage of a pressure pulse in its resonant range, like a wave guide. Astonishingly, it has been shown that a tube with a lumen diameter of about 0.2 mm permits such a pressure pulse to pass substantially unattenuated over a length of about 2 m, with adequate rate of rise and adequate pressure.

Preferably the tube, provided with a nozzle where appropriate, together with a fluid reservoir to store relatively large amounts of fluid to be injected during a prolonged period of use or prolonged surgery, is constructed as a sterile injection unit that can be operated as a unit. This construction makes it possible to prepare and perform an injection with minimal manipulation and in an extremely short time, even during an endoscopic operation for which the need of injection was unforeseen. Here it is especially advantageous for the injection unit to be constructed as an item of equipment to be used only once, so as to ensure that there is no deterioration due to wear and tear (blockages or the like) and that no unsterile units are used.

The injection unit preferably comprises at least part of the pump mechanism. One possibility is to equip the pump mechanism with a membrane, a piston or similar movable element as the pressure-generating component, which closes off the fluid reservoir or an intermediate reservoir in the tube in a water-tight manner. To move the membrane or generate the pressure, there can be provided a (disposable) device that is likewise fixedly attached to the whole unit, but preferably a separate, reusable drive mechanism, which applies to the piston or the membrane an adjustable pumping force. For this purpose a suitable pulse generator is provided.

Preferred embodiments of the invention will be come apparent from the subordinate claims.

In the following the invention is described in more detail with reference to drawings, wherein FIGS. 1A to 1P show various embodiments of tube ends;

DETAILED DESCRIPTION OF THE DRAWINGS

In the following description the same reference numerals are used for identical parts and parts with identical actions.

The method presented here and the apparatus presented here are designed for the injection of a great variety of liquids during endoscopic operations. A major problem with such injections is that the manipulation is difficult and laborious, and in particular requires a high degree of experience. When injection is performed with a needle, it is necessary not only to find the point on the tissue surface at which the fluid (marking liquid, medication, saline solution etc.) is to be applied but also to insert the needle to a particular depth. Only then can the actual application of the fluid be carried out, which in itself demands a delicate and responsive touch. That is, in addition to the two-dimensional "aiming" the third dimension (penetration depth) and the amount injected must be controlled.

Figure 1A:
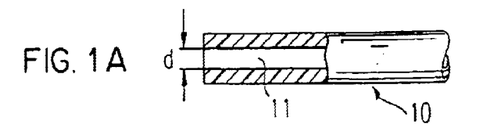
Figure 1B:
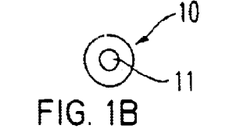

When the apparatus in accordance with the invention is used, by means of a pump mechanism the fluid can be expelled through a tube 10 shown in FIGS. 1A and 1B, i.e. through its lumen 11, with sufficiently high velocity that it penetrates the tissue. The depth of penetration in turn depends on how large the diameter d of the lumen 11 of the tube 10 is, and on the speed with which the fluid is expelled. Other parameters, such as the distance between the tube 10 and the tissue surface, also play a role.

Figure 1C:
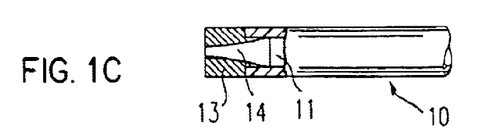
Figure 1D:
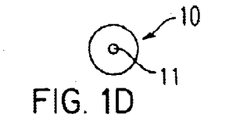
Figure 1E:
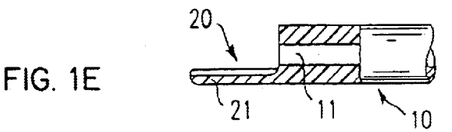
Figure 1F:
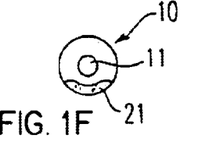

In the variant shown in FIGS. 1C and 1D, a nozzle 13 is provided in the end of the tube 10, which forms the terminal section 14 of the lumen 11 of the tube 10, the diameter of which decreases toward the opening in a substantially exponential manner. This particular slope makes it possible to "concentrate" the pressure pulse arriving through the lumen 11 substantially without loss, and thus to raise the velocity of the flowing fluid.

Figure 1G:
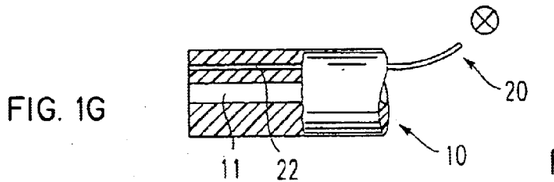
Figure 1H:
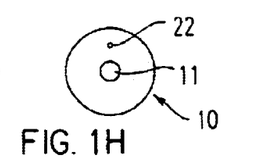

In the embodiment of the invention shown in FIGS. 1G and 1H, the tube 10 comprises at its end an aiming device 20, which here has the form of a "distance finger". With this finger the operator can not only better judge the distance between the tube 10 and the tissue surface, he can also better estimate the site at which the expelled fluid is expected to strike the tissue.

In the further embodiment of the invention shown in FIGS. 1G and 1H, there is incorporated into the tube 10 an optical fibre 22 that constitutes the aiming device 20. The end surface of the optical fibre 22 is so constructed that the (laser) light emitted from it is a substantially linear beam, a "light pointer" that strikes the surface of the tissue at a place substantially coincident with the site into which the fluid will be injected.

Figure 1I:
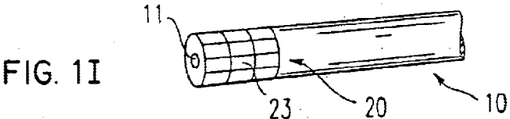
Figure 1J:
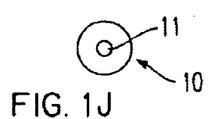

In the embodiment of the invention shown in FIGS. 1I and 1J the aiming device 20 comprises markings 23 on the terminal section of the tube 10. These markings 23 are within the field of view of the endoscope optics and make it easier for the user to make estimates of distance and/or direction. The various measures just described can of course also be combined with one another.

Figure 1K:
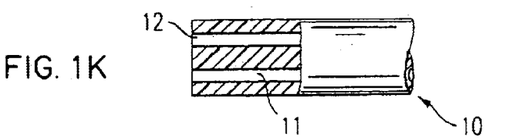
Figure 1L:
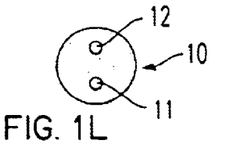

In the embodiment of the invention shown in FIGS. 1K and 1L the tube 10 is constructed with two lumina 11 and 12. These two lumina 11 and 12 can either serve to inject two different fluids—in which case they are connected to two pump mechanisms of the same kind—or one lumen 11 can be used for injection and the other lumen 12 for suction. It is of course also possible to use the one lumen for injecting fluids and the other for rinsing.

In the embodiment of the invention shown in FIGS. 1M and 1N, again two lumina 11 and 12 are provided in the tube 10, but these open into a common terminal section 14. This arrangement preferably serves either of two purposes, first to allow two fluids, expelled together through the lumina 11 and 12, to be mixed in the terminal section 14 before injection of this mixture. However, it is also possible to expel individual quanta of fluid in very rapid alternation through the lumina 11 and 12, so that these quanta are expelled in succession through the terminal section 14, enter the same hole in the tissue, and become mixed within the tissue.

Figures 1M, 1N, 1O, 1P:
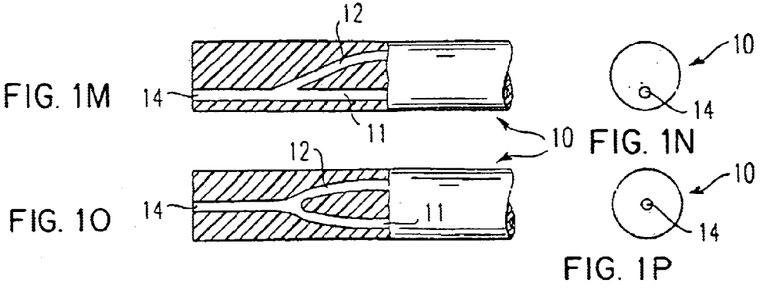

The embodiment shown in FIGS. 1O and 1P differs from that according to FIGS. 1M and 1N merely in that the terminal section 14 is disposed symmetrically with respect to the two lumina 11 and 12. Both this embodiment and that shown in FIGS. 1M and 1N are further suitable for using the one lumen 11 to inject fluid and the other lumen 12 to suck fluid away. For example, when an operation field is to be marked by tattooing, it is essential that the tattooing fluid not emerge before the intended time. On the other hand, the lumen 11 of the tube 10 must be essentially completely full if a pressure pulse suitable for injection is to be sent through the tube 10, which is often of a not inconsiderable length (1 to 2 m). Therefore, to keep the tube full, fluid is first allowed to flow slowly through the one lumen 11 while the proximal end of the second lumen 12 is attached to a low-pressure source. As soon as the fluid emerges from the proximal end of the second lumen 12, it is clear that the tube is adequately filled. The suction can then be continued, so that air (or liquid) from the operation site enters the distal end 14 and is sucked away through the lumen 12. The lumen 11 will nevertheless remain full, because fluid is no longer flowing through it. Now, as soon as a pressure pulse is applied to the proximal end of the lumen 11, a corresponding portion of fluid "shoots" out of the distal end 14 of the tube 10 and penetrates into the tissue.

It is particularly advantageous for the entire arrangement to be constructed as a single element that can be operated as a unit, wherein the fluid to be applied is stored in a pump mechanism and the pump mechanism is fixedly attached to the tube. Furthermore, the entire arrangement is sterile. It is thus possible to perform an injection very rapidly whenever it is required, without having to make special preparations for each operation. The arrangement corresponds, as it were, to a pre-filled disposable injection syringe.

Figure 2:
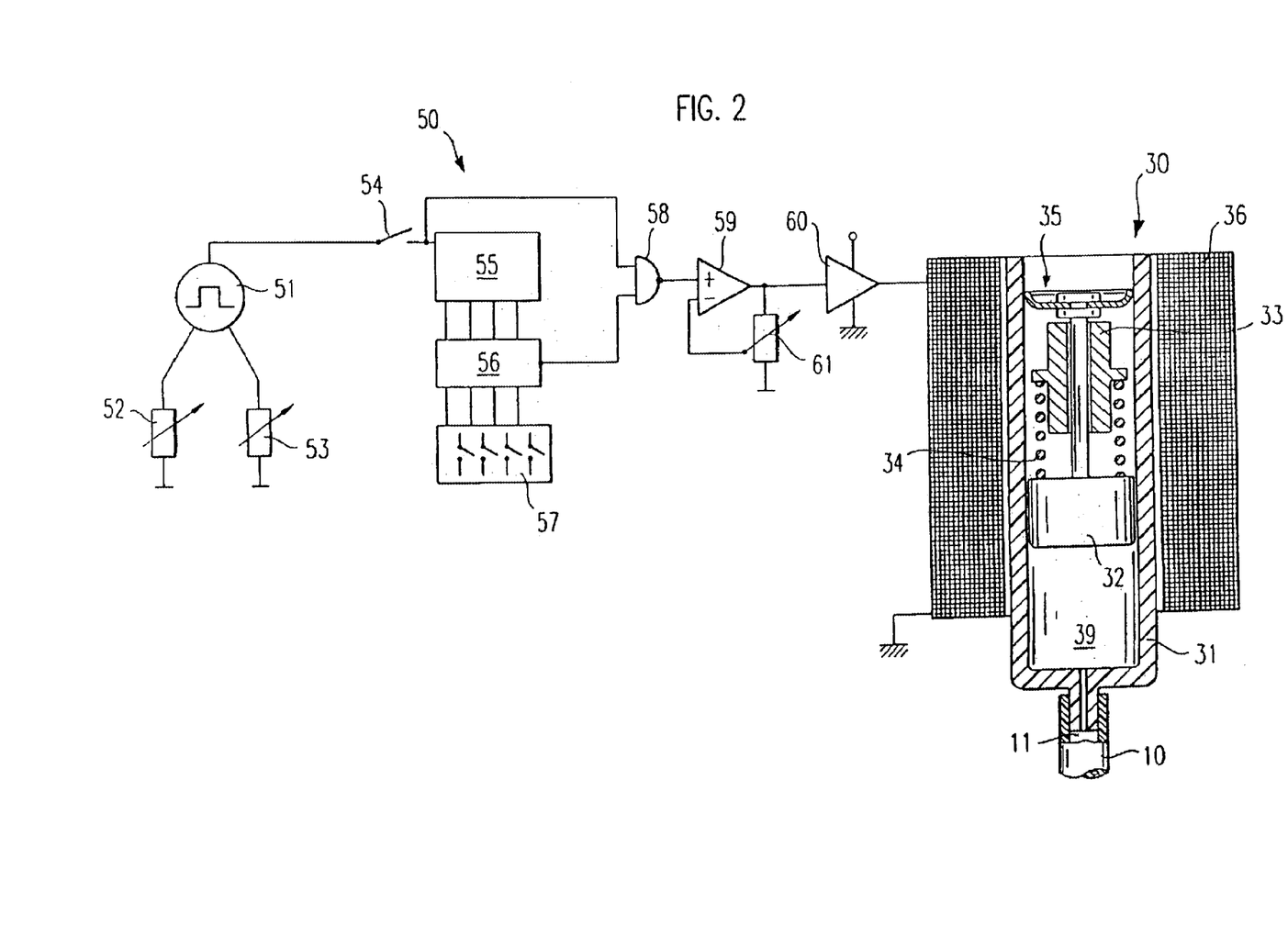
FIG. 2 is a schematic drawing of a pump mechanism with control circuit.

For this purpose the embodiment of the invention shown in FIG. 2 comprises a cylinder 31 to which the tube 10 is attached, and which contains in its interior a fluid reservoir 38 which at one end communicates with the lumen 11 of the tube 10 and at the other end is closed off by a piston 32.

The piston 32 comprises at its back end, away from the tube 10, a narrowed section on which a hammer 33 in the form of a cylindrical sheath is disposed so as to be axially displaceable against the force of a spring 34, such that the hammer 33 can be accelerated against the force of the spring 34 so as to strike the thickened part of the piston 32, imparting to the latter a forward impulse which in turn is transmitted as a pressure pulse to the fluid within the reservoir 39.

At the opposite end of the piston 32 is a barrier 35 to prevent the piston 32 from sliding back; that is, the piston 32 can move in only one direction, namely such as to reduce the volume of the fluid reservoir 39. The hammer 33 is made of a magnetizable material, whereas all other components of this arrangement are not magnetizable.

Around the circumference of the cylinder 31 is disposed a coil 36, the ends of its winding being connected to the output of a power amplifier 60. When a control signal is sent to the amplifier 60, a current flows through the coil 36 and thereby accelerates the hammer 33 towards the piston 32, which it strikes. If the control signal is appropriately pulse-shaped, the magnetic field will already be decaying shortly before the hammer 33 strikes the piston 32.

The signal driving the power amplifier 60 is provided by a control circuit 50, which on its input side comprises a control generator 51 that produces substantially rectangular pulses, the duration of which is determined by a first adjustment element 52 and the repetition rate of which is determined by a second adjustment element 53. The numeral 54 identifies a starting switch, which transmits the pulses generated (with specified duration and frequency) by the generator 51 to a counter 55, the content of which is communicated to a comparator 56 by suitable connecting leads. The comparator 56 compares the content of the counter 55 with a predetermined value provided by a pre-selector 57. As soon as the value of the counter 55 matches that of the preselector 57, the output signal from the generator, which until the match occurred had been passed through a NAND gate 58 to one input of an amplifier 59, is blocked. This means that after the key 54 has been pressed (which simultaneously resets the counter 55, as will be familiar to specialists), a number of pulses predetermined by the preselector 57 are sent to the input of the amplifier 59 and are passed on, with an amplitude predetermined by an amplitude adjustment device 61, to the input of the power amplifier 60, which in turn allows a current corresponding to the input signal to flow through the coil 36. That is, by controlling the electrical quantities and hence controlling the parameters of the force that accelerates the piston 32 and the number of individual pulses impinging on the piston 32, it is possible to determine the amount of fluid injected (in individual quanta) and the depth of the injection.

Figure 3:
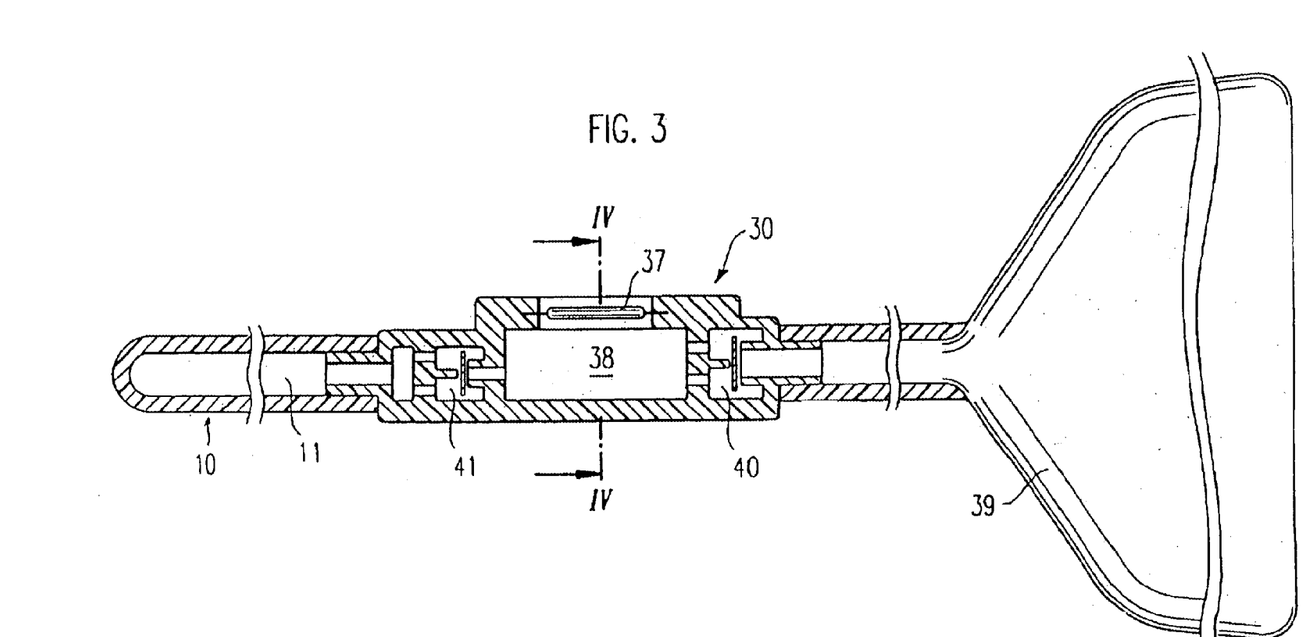
FIG. 3 shows a schematic longitudinal section of another preferred embodiment of an injection apparatus with pump mechanism.
Figure 4:
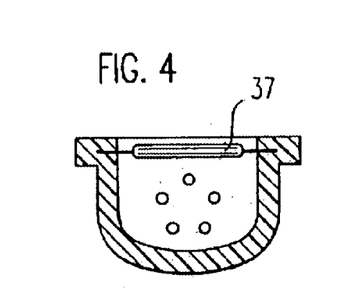
FIG. 4 shows a section along the line IV—IV in FIG. 3.
Figure 5:
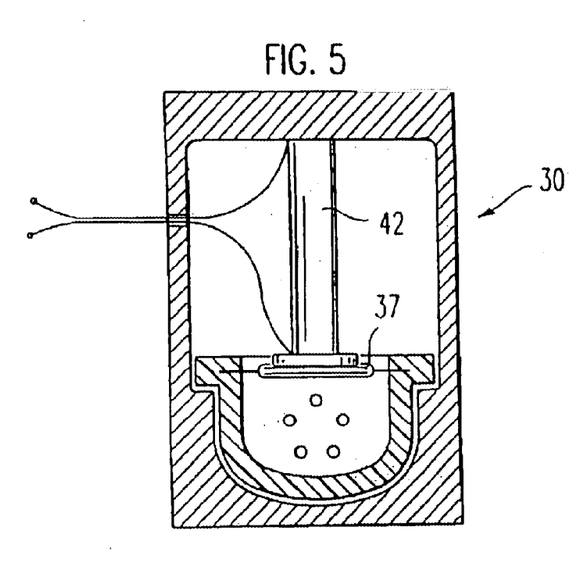
FIG. 5 shows a drive device for the pump mechanism according to FIGS. 3 and 4.

In the variant shown in FIG. 3, instead of a piston a membrane 37 is provided in the pump mechanism 30. This membrane closes off a pump space 38, which communicates by way of a first nonreturn valve 40 with a fluid reservoir 39 and by way of a second nonreturn valve 41 with the lumen 11 of a tube 10. The nonreturn valves 40 and 41 here are so constructed that fluid from the reservoir can flow into the lumen 11 of the tube 10 but not in the reverse direction. As indicated in FIGS. 3 and 4, the pump mechanism 30, the fluid reservoir 39 and the tube 10 together form a unit that can be operated as a whole, a one-way system. In order to impose the pressure pulses mentioned above, the membrane 37 must be moved. A piezo drive 42 as shown in FIG. 5, for example, can be used for this purpose. Because of the extremely high limiting frequency of such a system, it is not necessary to produce an actual "stroke"; when it receives an impulse with a suitably steep rising flank, the piezo crystal very rapidly expands the electrical power applied to it and can communicate a corresponding pressure pulse to the fluid in the pump space 38 by way of the membrane 37. An appropriately constructed electrodynamic system would be able to achieve the same result.

Figure 6:
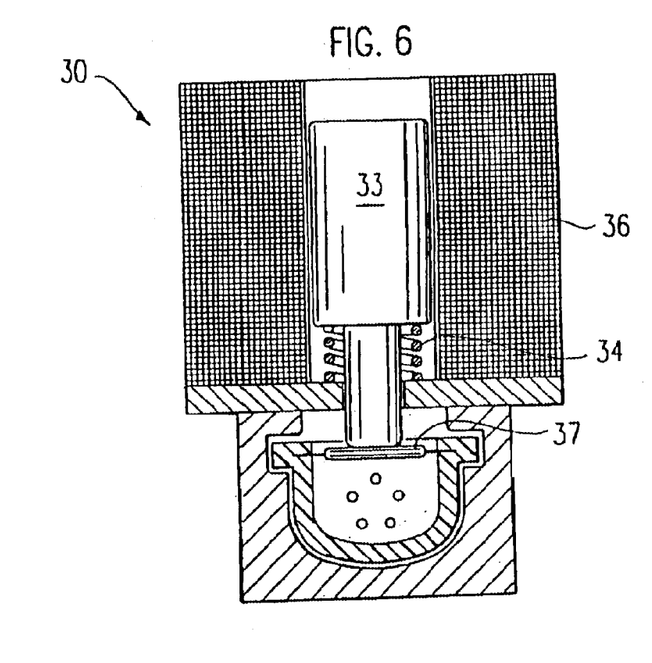
FIG. 6 shows another embodiment of a drive device for the pump mechanism according to FIGS. 3 and 4.

The drive shown in FIG. 6 is again an electromagnetic drive system like that according to FIG. 2, in which a hammer 33 is accelerated against the force of a spring 34 by the electromagnetic force of a coil 36 and strikes the membrane 37, so that a pressure pulse is conducted into the fluid contained in the pump space 38 below the membrane 37. The embodiments shown in FIGS. 5 and 6 can be controlled by a control circuit 50, such as was described with reference to FIG. 2.

Figure 7:
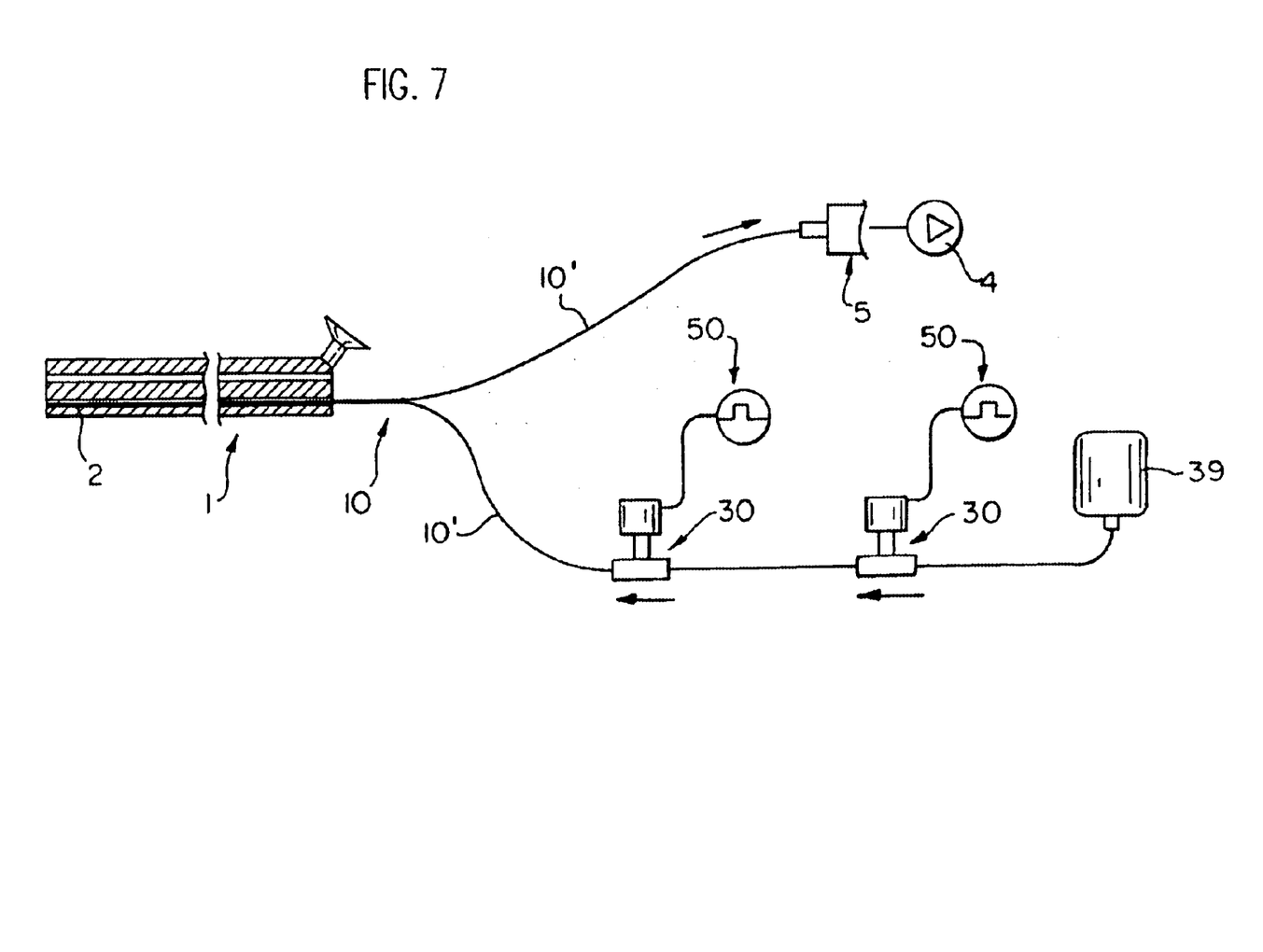
FIG. 7 is a schematic drawing of another embodiment of the injection apparatus.

The entire system, in a preferred embodiment of the invention, now appears as shown in FIG. 7. The reference numeral 1 indicates an endoscope, through the working channel 2 of which the tube 10 has been inserted. The tube 10 in this case has two lumina and is divided into two individual sections 10' and 10" (each with one lumen), such that the one section 101 leads to a pump mechanism 30 that sucks fluid out of a reservoir 39 and—under the control of a controller 50—can inject a corresponding number of fluid quanta into a tissue. The other tube section 10" is in communication with a suction source 4 by way of a push-on connector 5. As a result, when the endoscope 1 is bent during manipulation and the volume of the tube 10 therefore changes, any fluid in the terminal section of the tube 10 that might otherwise be thus caused to emerge through the end of the tube 10 will instead be sucked away.

List of Reference Numerals

1 Endoscope
2 Working channel
4 Suction source
5 Push-on connector
10 Tube
11 Lumen
12 Lumen
13 Nozzle
14 Terminal section
20 Aiming device
21 Distance finger
22 Optical fibre
23 Marking
30 Pump mechanism
31 Cylinder
32 Piston
33 Hammer
34 Spring
35 Barrier to backward movement
36 Coil
37 Membrane
38 Pump space
39 Fluid reservoir
40 First nonreturn valve
41 Second nonreturn valve
42 Piezo drive
50 Control circuit
51 Control generator
52 Duration adjustor
53 Repetition-rate adjustor
54 Starting switch
55 Counter
56 Comparator
57 Preselector
58 NAND gate
59 Settings amplifier
60 Power amplifier
61 Amplitude adjustor

What is claimed is:

1. Method of endoscopically injecting a defined amount of at least one fluid, in particular a solution, suspension or emulsion, into a tissue of a hollow organ, a body cavity or an artificial cavity in a human or animal body, in which a specified amount of fluid is expelled out of an end of a tube or a nozzle with hydraulic parameters i.e. pressure, rate of pressure increase, duration and/or velocity are adjusted to specified values for providing an energy of said fluid such that, after traveling a distance between the end of the tube or the nozzle and the tissue in substantially free flight, the fluid penetrates into the tissue and remains within said tissue wherein to inject relatively large amounts of fluid, a plurality of substantially equal-sized minimal quantities or fluid quanta is injected, wherein the fluid is injected at an angle of about 30° to 60° with respect to the tissue or to its surface.

2. Method according to claim 1 wherein the fluid is injected in such a thin stream that a hole created in the tissue during injection closes thereafter itself, without previously allowing an appreciable amount of injected fluid to escape.

3. Method according to claim 1, wherein two different fluids that react with one another, such as fibrin adhesive, either are mixed shortly before being injected together or are injected in rapid succession into the same site in the tissue so that they become mixed at the injection site.

4. Method of endoscopically injecting a defined amount of at least one fluid, in particular a solution, suspension or emulsion, into a tissue of a hollow organ, a body cavity or an artificial cavity in a human or animal body, in which a specified amount of fluid is expelled out of an end of a tube or a nozzle with hydraulic parameters i.e. pressure, rate of pressure increase, duration and/or velocity are adjusted to specified values for providing an energy of said fluid such that, after traveling a distance between the end of the tube or the nozzle and the tissue in substantially free flight, the fluid penetrates into the tissue and remains within said tissue wherein to inject relatively large amounts of fluid, a plurality of substantially equal-sized minimal quantities or fluid quanta is injected, and wherein fluid that emerges slowly and unintentionally from the end of the tube is removed by suction, and wherein a continuous current of fluid is removed by suction, in such a way that the volume of fluid removed by suction per unit time is less than the volume injected per unit time during the injection process.

* * * * *